(12) United States Patent
Kim et al.

(10) Patent No.: US 11,426,426 B2
(45) Date of Patent: Aug. 30, 2022

(54) PHARMACEUTICAL COMPOSITION FOR PREVENTING OR TREATING INFLAMMATORY DISEASES, CONTAINING NITROGEN MONOXIDE-SENSITIVE ACRYLAMIDE-BASED POLYMER

(71) Applicant: POSTECH ACADEMY-INDUSTRY FOUNDATION, Pohang-si (KR)

(72) Inventors: Won Jong Kim, Pohang-si (KR); Ji Won Yeo, Busan (KR)

(73) Assignee: POSTECH ACADEMY-INDUSTRY FOUNDATION, Pohang-si (KR)

( * ) Notice: Subject to any disclaimer, the term of this patent is extended or adjusted under 35 U.S.C. 154(b) by 0 days.

(21) Appl. No.: 17/182,504

(22) Filed: Feb. 23, 2021

(65) Prior Publication Data

US 2021/0275574 A1 Sep. 9, 2021

Related U.S. Application Data

(63) Continuation of application No. PCT/KR2018/011902, filed on Oct. 10, 2018.

(30) Foreign Application Priority Data

Aug. 30, 2018 (KR) .................. 10-2018-0102615

(51) Int. Cl.
*A61K 31/785* (2006.01)
*A61K 9/00* (2006.01)
*A61K 9/06* (2006.01)

(52) U.S. Cl.
CPC .......... *A61K 31/785* (2013.01); *A61K 9/0019* (2013.01); *A61K 9/06* (2013.01)

(58) Field of Classification Search
CPC ...... A61K 31/785; A61K 9/0019; A61K 9/06; A61K 9/5146; A61K 45/06; A61K 47/18; A61K 47/32; A61P 29/00
See application file for complete search history.

(56) References Cited

U.S. PATENT DOCUMENTS

| 5,767,103 | A | * | 6/1998 | Greenberg | ........... | A61K 31/714 |
| | | | | | | 514/52 |
| 7,022,313 | B2 | * | 4/2006 | O'Connor | ............ | A61K 9/0021 |
| | | | | | | 424/501 |

FOREIGN PATENT DOCUMENTS

| EP | 2272881 | 1/2011 | | |
| JP | 2009 529668 | 8/2009 | | |
| JP | 2011513424 | 4/2011 | | |
| JP | 2013234205 | 11/2013 | | |
| KR | 10 2011 0005798 | 1/2011 | | |
| WO | WO-0216453 A1 | * | 2/2002 | ............. A61L 27/16 |

OTHER PUBLICATIONS

Davis, Angew Chem Int Ed, Polymers Responsive Nitric Oxide (Year: 2014).*
Junghong Park et al., "Therapeutic-Gas-Responsive Hydrogel", Adv Mater. Nov. 2017;29(44). doi: 10.1002/adma.201702859. Epub Oct. 11, 2017. PMID: 29024110.
Mahmoud A Hussein et al., "Role of cross-linking process on the performance of PMMA", International Journal of Biosensors & Bioelectronics (2017) 3(3), DOI: 10.15406/ijbsbe.2017.03.00065.
Honor Whiteman, "Rheumatoid arthritis could be treated with a novel hydrogel", Medical News Today, Oct. 13, 2017.
Jung Hong Park et al., "Design of nitric oxide-responsive hydrogel", The 119th General Meeting of the Korean Chemical Society, Apr. 19, 2017-Apr. 21, 2017.
JPO, Office Action of JP 2021-510801 dated Mar. 15, 2022.
Honor Whiteman, "Rheumatoid arthritis could be treated with a novel hydrogel", Medical News Today, Oct. 13, 2017, [online].
Junghong Park et al., "Therapeutic-Gas-Responsive Hydrogel", Advanced Matelials, 2017, vol. 29, Article No. 1702859, Oct. 11, 2017.

* cited by examiner

*Primary Examiner* — Matthew P Coughlin
*Assistant Examiner* — Thurman Wheeler
(74) *Attorney, Agent, or Firm* — Lex IP Meister, PLLC

(57) ABSTRACT

The invention relates to a nitric oxide-responsive acrylamide-based polymer, and more particularly, to an acrylamide-based polymer that is produced using an acrylamide-based monomer and a nitric oxide-sensitive crosslinking agent and allows prevention or treatment of a disease or illness caused by overexpression of nitric oxide.

9 Claims, 9 Drawing Sheets

[Fig. 1]
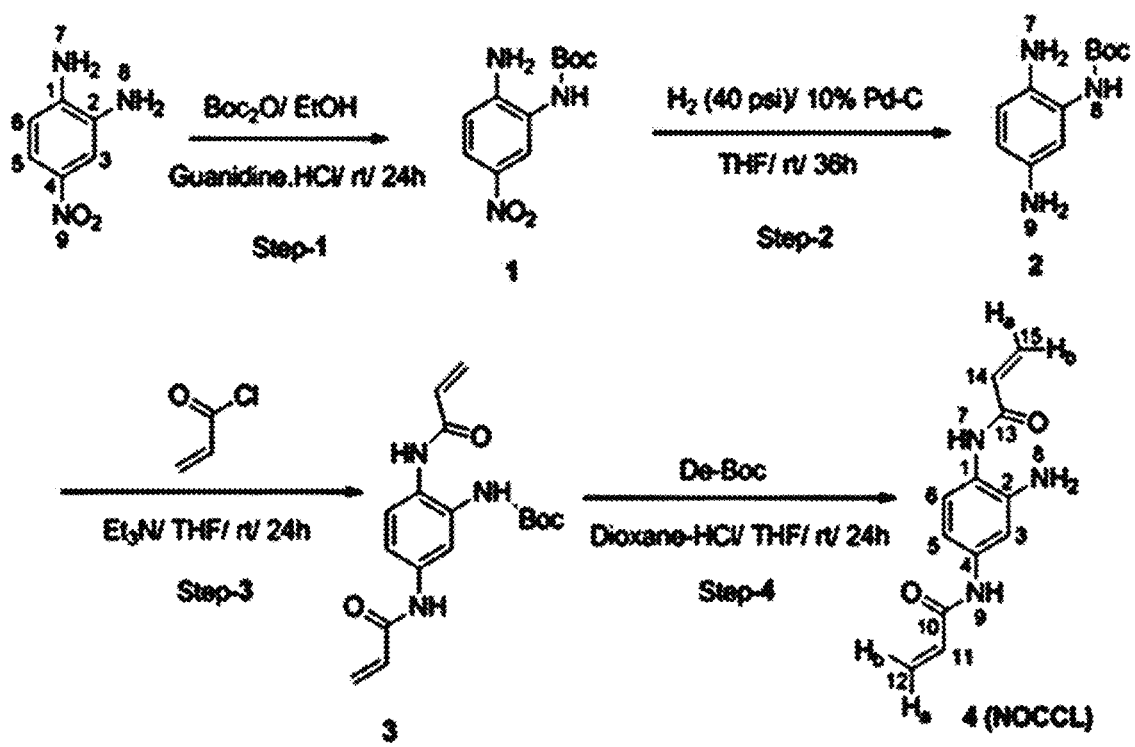

[Fig. 2]
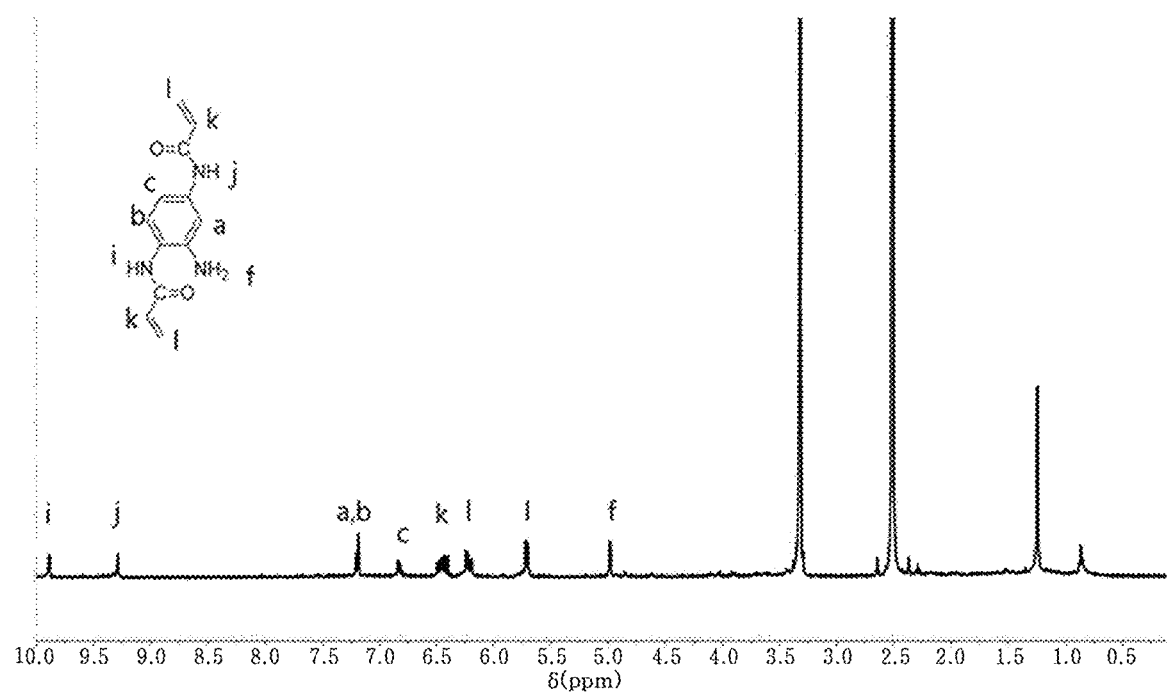

[Fig. 3]
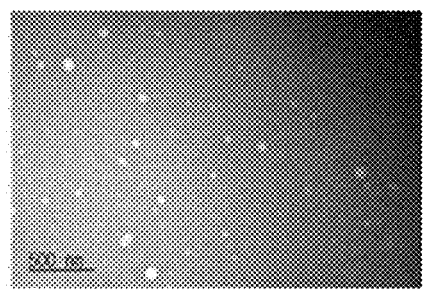
**EXAMPLE 1
(in watet)**
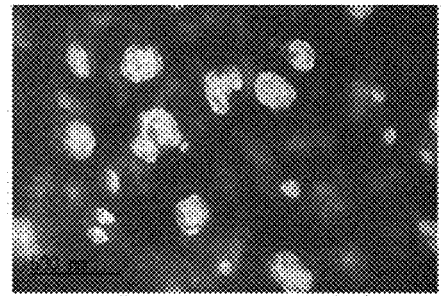
**EXAMPLE 1
(in NO solution)**
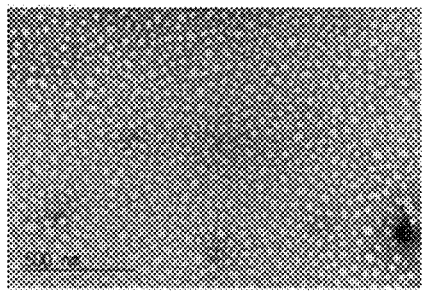
**COMPARATIVE
EXAMPLE 1
(in watet)**
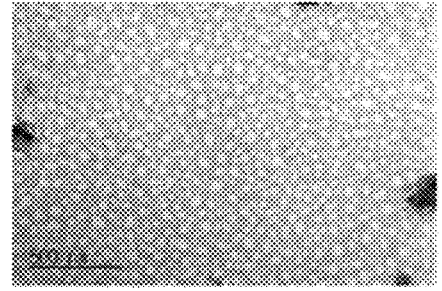
**COMPARATIVE
EXAMPLE 1
(in NO solution)**

[Fig. 4]
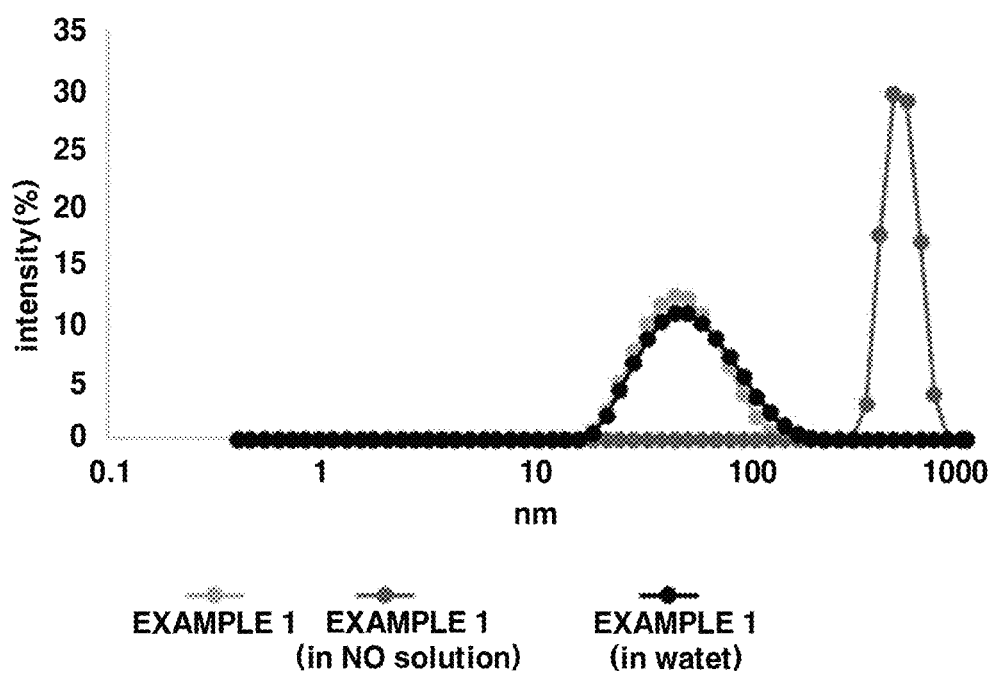

[Fig. 5(a)]
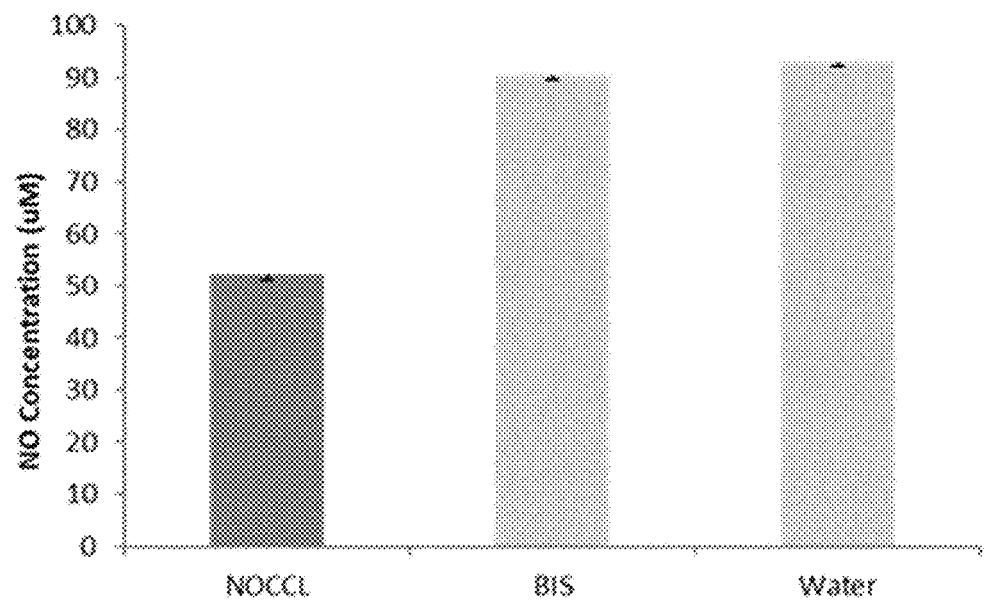
[Fig. 5(b)]
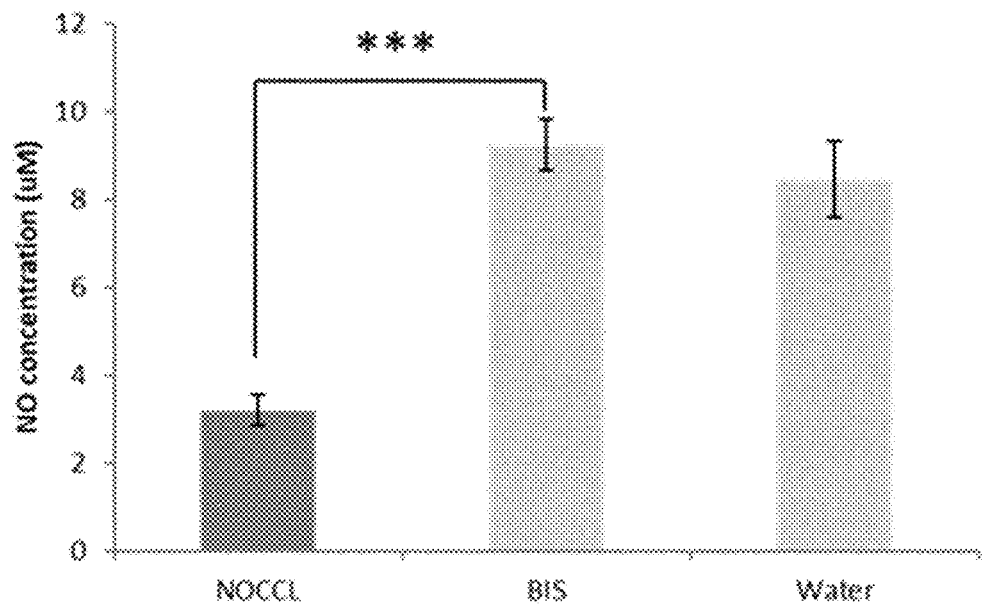

[Fig. 6]
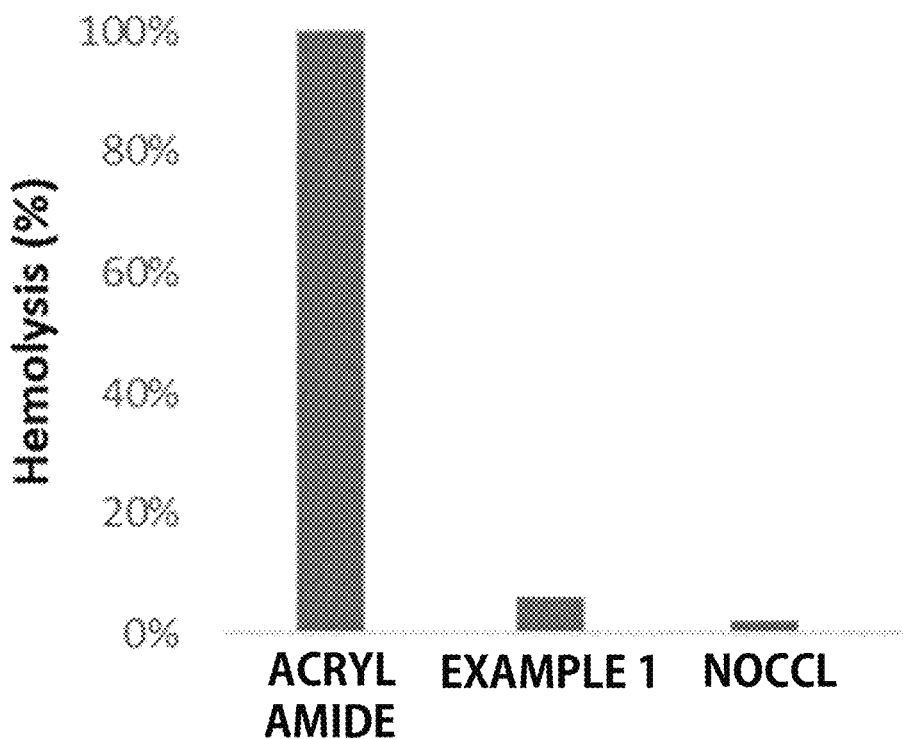

[Fig. 7(a)]
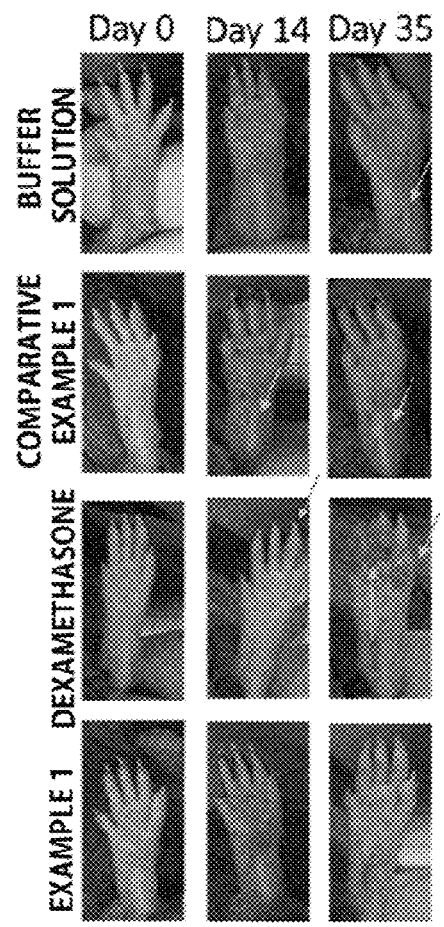

[Fig. 7(b)]
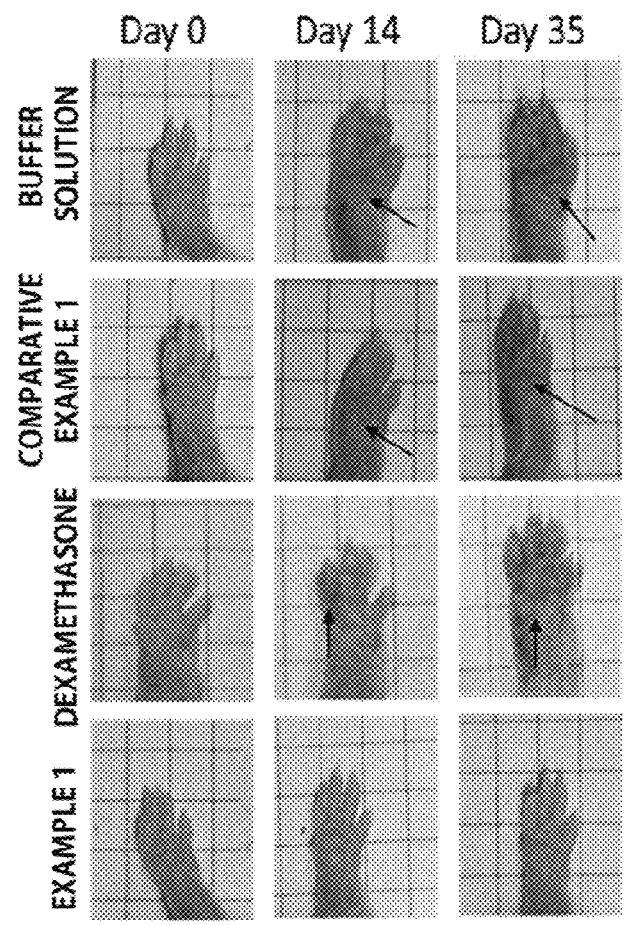

[Fig. 8]
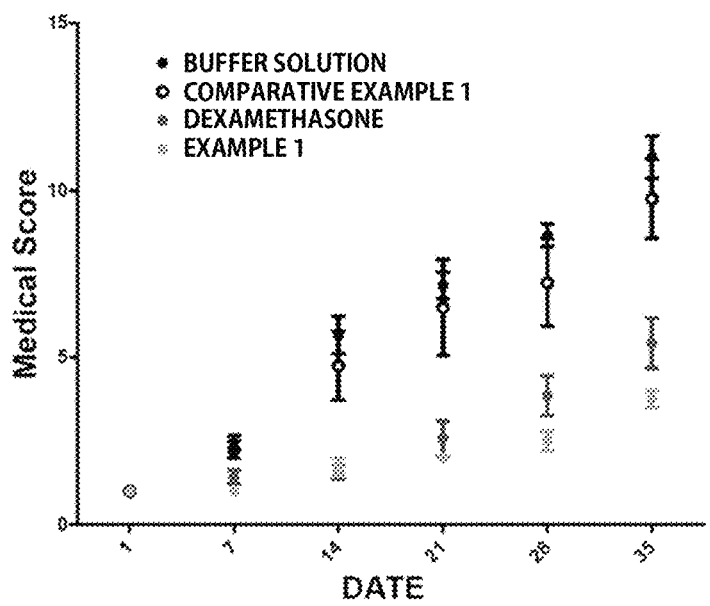

PHARMACEUTICAL COMPOSITION FOR PREVENTING OR TREATING INFLAMMATORY DISEASES, CONTAINING NITROGEN MONOXIDE-SENSITIVE ACRYLAMIDE-BASED POLYMER

TECHNICAL FIELD

This application claims priority from Korean Patent Application No. 10-2018-0102615, filed on Aug. 30, 2018, the entire disclosure of which is incorporated herein by reference.

The present invention relates to a pharmaceutical composition for preventing or treating an inflammatory disease including a nitric oxide-sensitive acrylamide-based polymer, and more particularly, the invention relates to an acrylamide-based polymer that can be used for preventing or treating an inflammatory disease or illness developing due to overexpression of nitric oxide, the acrylamide-based polymer including a polymer produced by using an acrylamide-based monomer and a crosslinking agent responsive to nitric oxide.

BACKGROUND OF THE INVENTION

Nitric oxide is a highly reactive radical molecule having a short half-life of several seconds or less and is generated in various cells in the human body. Nitric oxide is known as a defense substance exhibiting anticancer and antimicrobial action for the immune system, as a neurotransmitter for the nerve system, and as a vasodilatory substance for the circulation system.

Thus, studies have been conducted on new substances and methods that can more efficiently release nitric oxide according to the purpose of use, in order to use nitric oxide for pharmaceutical use applications such as anticancer therapy.

However, when the immune system of living bodies collapses due to environmental pollution, stress, and the like, overactivated macrophages secrete large quantities of nitric oxide and thereby induce autoimmune diseases or inflammatory diseases.

Furthermore, since nitric oxide at high concentrations becomes toxic, in a case in which generally a large quantity of nitric oxide is released in the body, nitric oxide may rather adversely affect the body by causing rheumatoid arthritis, osteoarthritis, and inflammatory bowel syndrome.

Meanwhile, rheumatoid arthritis is a chronic inflammatory disease of unknown cause, which is characterized by polyarthritis. In the early stage, inflammation occurs in the synovial membrane wrapping the joint; however, inflammation gradually spreads to the surrounding cartilage and bones and causes destruction and deformation of the joint. Rheumatoid arthritis is a disease that can invade not only the joints but also the entire body by causing anemia, Sjogren syndrome, subcutaneous nodules, pulmonary fibrosis, vasculitis, skin ulcers, and the like, as extraarticular symptoms.

The exact cause for rheumatoid arthritis has not yet been clarified; however, it is known that autoimmune phenomena serve as an important mechanism. Autoimmunity is a phenomenon in which the immune system that protects the human body from external attacks goes awry and rather attacks the body itself. Generally, genetic predisposition, bacterial or viral infections, and the like are considered as the causes of rheumatoid arthritis. It is known that rheumatoid arthritis is likely to occur after a person is subjected to physical or mental stress. Furthermore, rheumatoid arthritis is an intractable autoimmune disease accompanied by tumefaction, inflammation, stiffening, and pain while exhibiting the pathological condition of systemic polyarthritis. That is, rheumatoid arthritis is a systemic disease in which the body itself misrecognizes oneself as nonself due to a failure of self-nonself discrimination, attacks self-tissues, and causes abnormal immune response, thereby inducing inflammation in the connective tissues.

Thus, in the environment of rheumatoid arthritis, nitric oxide exerts adverse influence by increasing cytokine-induced bone resorption of osteoclasts and promoting cell death at the joints.

Therefore, there is a demand for a novel therapeutic agent that is responsive to nitric oxide, which can aggravate autoimmune diseases or inflammatory diseases, can scavenge nitric oxide, and can thereby alleviate or treat a disease.

DETAILED DESCRIPTION OF THE INVENTION

Technical Problem

In order to solve problems such as described above, the inventors of the present invention produced a nitric oxide-sensitive acrylamide-based polymer and verified that such a polymer, which may be provided in a hydrogel form, is sensitively responsive to nitric oxide and is also capable of scavenging nitric oxide, and that the hydrogel can be easily administered into the body in the form of a nano-sized hydrogel and can prevent or treat an inflammatory disease which is presumed to develop in the presence of nitric oxide at a high concentration, thus completing the present invention.

Therefore, an object of the present invention is to provide a nitric oxide-sensitive acrylamide-based polymer capable of preventing or treating an inflammatory disease or illness caused by overexpression of nitric oxide.

Technical Solution

In order to achieve the above-described object, according to an aspect of the present invention, there is provided a pharmaceutical composition for preventing or treating an inflammatory disease, the pharmaceutical composition including a nitric oxide-sensitive acrylamide-based polymer.

The acrylamide-based polymer may be a polymer having a structure represented by the following Chemical Formula 2, which is produced using an acrylamide-based monomer, a crosslinking agent having a structure represented by the following Chemical Formula 1, a radical initiator, and a catalyst:

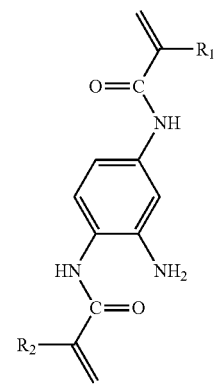

[Chemical Formula 1]

-continued

[Chemical Formula 2]

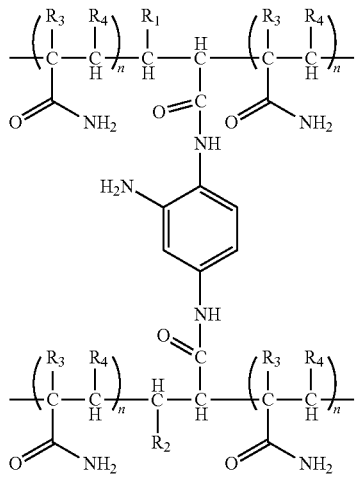

wherein $R_1$, $R_2$, $R_3$, and $R_4$ each independently represent a hydrogen atom or a C1-C10 substituted or unsubstituted alkyl group; and n represents an integer from 1 to 1,000.

According to an embodiment of the present invention, $R_1$, $R_2$, $R_3$, and $R_4$ may be each independently a hydrogen atom.

The acrylamide-based monomer may be any one or more selected from the group consisting of acrylamide, (meth) acrylamide, N-isopropylacrylamide, N-tertiary butyl acrylamide, 3-hydroxypropyl (meth)acrylamide, 4-hydroxybutyl (meth)acrylamide, 6-hydroxyhexyl (meth)acrylamide, 8-hydroxyoctyl (meth)acrylamide, 2-hydroxyethylhexyl (meth) acrylamide, N-methylol (meth)acrylamide, N,N-dimethylol (meth)acrylamide, N-methoxymethyl (meth)acrylamide, and N-propoxymethyl (meth)acrylamide.

The polymer may be in a hydrogel form, and at this time, the diameter of the hydrogel may be 10 nm to 500 nm.

According to an embodiment of the present invention, the pharmaceutical composition may be an injectable preparation.

The inflammatory disease may be a disease in which nitric oxide in the body exhibits a condition of overexpression.

The above-described inflammatory disease may be rheumatoid arthritis.

The pharmaceutical composition can further include a biologically active substance, and a nitric oxide-sensitive acrylamide-based polymer having a structure represented by the above-described Chemical Formula 2 can carry the biologically active substance.

Effects of the Invention

The pharmaceutical composition for preventing or treating an inflammatory disease including a nitric oxide-sensitive acrylamide-based polymer according to embodiments of the present invention is responsive to nitric oxide and is also capable of scavenging nitric oxide.

Furthermore, the pharmaceutical composition for preventing or treating an inflammatory disease including a nitric oxide-sensitive acrylamide-based polymer according to embodiments of the present invention can prevent or treat a disease or illness caused by overexpression of nitric oxide.

The pharmaceutical composition for preventing or treating an inflammatory disease including a nitric oxide-sensitive acrylamide-based polymer according to embodiments of the present invention, which is in the form of a nano-sized hydrogel, can be easily administered into the body, is highly hydrophilic, and has excellent biocompatibility.

BRIEF DESCRIPTION OF THE DRAWINGS

FIG. 1 is a reaction diagram for a nitric oxide-cleavable crosslinker (NOCCL) according to an embodiment of the present invention.

FIG. 2 is a $^1$H-NMR spectrum of the nitric oxide-cleavable crosslinker (NOCCL) according to an embodiment of the present invention.

FIG. 3 is a set of TEM images obtained before and after treating Example 1 according to an embodiment of the present invention and Comparative Example 1 with a nitric oxide solution.

FIG. 4 is a graph showing the results for dynamic light scattering (DLS) obtained after treating Example 1 according to an embodiment of the present invention with a nitric oxide solution or water.

FIG. 5(a) and FIG. 5(b) are graphs showing the results obtained by treating a nitric oxide-cleavable crosslinker (NOCCL) according to an embodiment of the present invention and N,N'-methylene bisacrylamide (BIS) respectively with a 100 μM nitric oxide solution and a 10 μM nitric oxide solution, and checking the nitric oxide scavenging ability.

FIG. 6 is a graph showing the results for evaluating hemolysis of Example 1 according to an embodiment of the present invention, a nitric oxide-cleavable crosslinker (NOCCL), and an acrylamide monomer.

FIG. 7 is a set of photographs of the footpads of hindlimbs (FIG. 7a) and the footpads of forelimbs (FIG. 7b) of rheumatoid arthritis model animals, obtained by administering Example 1 according to an embodiment of the present invention, Comparative Example 1, dexamethasone, and a buffer solution to the animals and making observation of the animals.

FIG. 8 is a graph showing the results obtained by administering Example 1 according to an embodiment of the present invention, Comparative Example 1, dexamethasone, and a buffer solution to rheumatoid arthritis model animals for five weeks and evaluating the severity of articular inflammation over time.

BEST MODE

The present invention provides a pharmaceutical composition for preventing or treating an inflammatory disease including a nitric oxide-sensitive acrylamide-based polymer.

According to an embodiment of the present invention, the acrylamide-based polymer is a polymer having a structure represented by the following Chemical Formula 2, which is produced using an acrylamide-based monomer, a crosslinking agent having a structure represented by the following Chemical Formula 1, a radical initiator, and a catalyst:

[Chemical Formula 1]

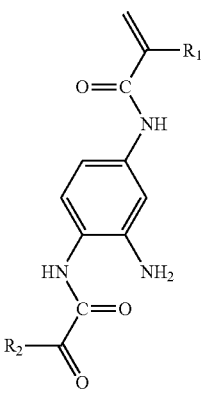

[Chemical Formula 2]

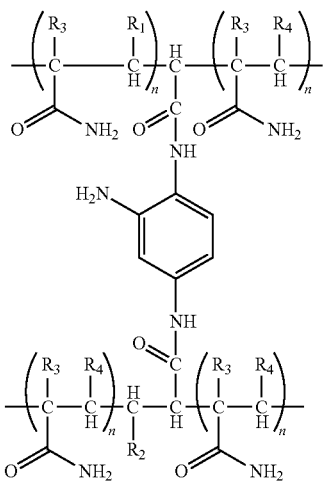

wherein $R_1$, $R_2$, $R_3$, and $R_4$ each independently represent a hydrogen atom or a C1-C10 substituted or unsubstituted alkyl group; and n represents an integer from 1 to 1,000.

The acrylamide-based monomer is a compound having a double bond and an amide functional group and is a monomer that can be polymerized by radical polymerization.

Furthermore, the acrylamide-based monomer may be any one or more selected from the group consisting of acrylamide, (meth)acrylamide, N-isopropylacrylamide, N-tertiary butyl acrylamide, 3-hydroxypropyl (meth)acrylamide, 4-hydroxybutyl (meth)acrylamide, 6-hydroxyhexyl (meth)acrylamide, 8-hydroxyoctyl (meth)acrylamide, 2-hydroxyethylhexyl (meth)acrylamide, N-methylol (meth)acrylamide, N,N-dimethylol (meth)acrylamide, N-methoxymethyl (meth)acrylamide, and N-propoxymethyl (meth)acrylamide. The acrylamide-based monomer is preferably acrylamide, (meth)acrylamide, or a combination thereof, and is more preferably acrylamide; however, the acrylamide-based monomer is not limited to these.

The physical and chemical properties of the polymer according to the present invention may vary depending on the chemical structure of the acrylamide-based monomer. For example, in the case of a polymer obtained by polymerizing an acrylamide-based monomer having a hydroxy group, the polymer acquires higher hydrophilicity as compared to a polymer obtained by polymerizing an acrylamide monomer, and when the polymer is formed into a hydrogel, the polymer can undergo swelling more easily and can absorb more water. On the other hand, in the case of a polymer obtained by polymerizing an acrylamide-based monomer having an alkyl group, the polymer acquires higher hydrophobicity as compared to a polymer obtained by polymerizing an acrylamide monomer and can therefore form a hydrogel having a smaller size.

The crosslinking agent is a crosslinking agent that can react with nitric oxide (nitric oxide-cleavable crosslinker) and is preferably a compound including an acrylamide group at both ends, which reacts with nitric oxide to produce an amide-substituted benzotriazole intermediate and is hydrolysable in an aqueous medium.

Furthermore, the crosslinking agent is responsive to nitric oxide and is capable of scavenging nitric oxide by reacting with nitric oxide. At this time, the crosslinking agent is preferably a compound containing an o-phenylenediamine moiety reacting with nitric oxide.

At this time, the compound containing an o-phenylenediamine moiety can form an amide-substituted benzotriazole intermediate residue as a result of a reaction with nitric oxide, and this intermediate residue can be hydrolyzed to be decomposed into a benzotriazole residue and a carboxylic acid residue.

The crosslinking agent can be synthesized as shown in FIG. 1. According to FIG. 1, the crosslinking agent can be synthesized by a four-stage course. To explain the synthesis by using 4-nitro-o-phenylenediamine as a starting material, the first stage is a stage of protecting an amino group at C-2 of 4-nitro-o-phenylenediamine with a protective group such as a Fmoc group or a Boc group. The second stage is a stage of reducing $4\text{-}NO_2$ of 4-nitro-o-phenylenediamine into $4\text{-}NH_2$. Next, the third stage is a stage of bonding two amino groups at C-1 and C-4 with acryloyl chloride to form acrylamide, and lastly, the fourth stage is a stage of removing the protective group at C-2. The solvent or catalyst used in the fourth stage are not particularly limited so long as the solvent or catalyst is generally used in the pertinent art.

The crosslinking agent has a structure represented by the above-described Chemical Formula 1, and here, $R_1$ and $R_2$ each independently represent a hydrogen atom or a C1-C10 substituted or unsubstituted alkyl group. The alkyl group may be a linear group, a branched group, or a cyclic group. Preferably, $R_1$ and $R_2$ each independently represent a hydrogen atom; however, $R_1$ and $R_2$ are not limited to this.

The radical initiator is a compound generating a radical and causes a polymerization initiation reaction by bonding to a double bond moiety of the acrylamide monomer.

The radical initiator may be an oil-soluble radical initiator, a water-soluble radical initiator, or an oxidation-reduction initiator, and preferably, the radical initiator is a water-soluble radical initiator; however, the radical initiator is not limited to this. At this time, as the water-soluble radical initiator, ammonium persulfate, potassium persulfate, or sodium persulfate can be used alone or can be used in combination with a reducing agent such as sodium bisulfate or sodium formaldehyde sulfoxylate. On the other hand, as the oil-soluble radical initiator, amino persulfate, lauroyl peroxide, hydrogen peroxide, benzoyl peroxide, acetyl peroxide, azobisisobutyronitrile, t-butyl hydroperoxide, dibutyl peroxide, benzoyl hydroperoxide, perbenzoic acid, peracetic acid, and the like are used, and these may be used singly or in combination with the above-described reducing agents.

The catalyst plays the role of an accelerator or the role of a free radical stabilizer during the production of a free radical from a radical initiator, and the catalyst may be a polar additive.

Here, an example of the polar additive is a base, and another example thereof is a compound having an amine group and is selected from the group consisting of trimethylamine, triethylamine, tripropylamine, and tetramethylethylenediamine. The polar additive is preferably triethylamine or tetramethylethylenediamine; however, the polar additive is not limited to this.

The polymer according to the present invention may be a polymer in which repeating units of the acrylamide-based monomer and the crosslinking agent are arranged randomly, alternatingly, or sequentially, and the polymer may be a crosslinked polymer or a branched polymer.

The polymer according to the present invention is a chemically crosslinked polymer in which, as can be seen in Chemical Formula 2, the acrylamide-based monomer forms the backbone of the polymer, and the crosslinking agent serves as a linker between backbones.

$R_3$ and $R_4$ each independently represent a hydrogen atom or a C1-C10 substituted or unsubstituted alkyl group. The alkyl group may be a linear group, a branched group, or a cyclic group. Preferably, $R_3$ and $R_4$ each independently represent a hydrogen atom; however, $R_3$ and $R_4$ are not limited to this.

The n represents an integer from 1 to 1,000 and is preferably 30 to 500; however, n is not limited to this.

The polymer according to the present invention can be produced into a crosslinked polymer within several minutes by mixing all of the above-described acrylamide-based monomer, a crosslinking agent having a structure of Chemical Formula 1, a radical initiator, and a catalyst. As such, the method for producing the polymer is very simple with high yield, and the manufacturing cost for the production process is low, and production in large quantities is possible.

In this case, the temperature upon mixing in the method for producing the polymer may be normal temperature, which may be 15° C. to 25° C.

The polymer according to the present invention may have a weight average molecular weight (Mw) in the range of 2,000 to 50,000. The weight average molecular weight as used in the present specification may be, for example, a value measured using gel permeation chromatography (GPC) and calculated relative to polystyrene standards, and unless particularly stated otherwise, the term molecular weight may refer to weight average molecular weight. The molecular weight (Mw) as described above may be useful in a case in which, for example, the above-described polymer is crosslinked to be produced into a hydrogel and is used in a pharmaceutical composition. By using the above-described polymer having a molecular weight (Mw) in the above-described range, the sensitivity to nitric oxide can be increased, and the polymer can react with a large amount of nitric oxide and scavenge nitric oxide.

According to an embodiment of the present invention, the polymer is crosslinked and can be formed into a hydrogel, and here, the hydrogel means a three-dimensional structure of a hydrophilic polymer retaining a sufficient amount of water. Therefore, the polymer is a polymer compound having a three-dimensional crosslinked structure and may be in the form of a hydrogel that has absorbed water and swollen under the conditions where water is present.

In this case, the above-described hydrogel is a nano-sized hydrogel in a 100% swollen state, and at this time, the diameter of the hydrogel may be 10 nm to 500 nm. The diameter is preferably 20 nm to 150 nm, and more preferably 30 nm to 70 nm. In a case in which the diameter of the hydrogel is less than 10 nm, the effect of scavenging nitric oxide is deteriorated, and in a case in which the diameter is more than 500 nm, administration into the body is not easily performed, while the retention time in the body may become too short, or the possibility of hemolysis may increase.

With regard to the polymer, the size of the hydrogel can be regulated by regulating the concentrations of the acrylamide-based monomer and the crosslinking agent.

Furthermore, with regard to the polymer, the mixing ratio of the acrylamide-based monomer and the crosslinking agent can be regulated according to the size, physical properties, and the like of the hydrogel to be produced.

The mixing ratio of the acrylamide-based monomer and the crosslinking agent may be 1,000:0.3 to 1.0 as a molar ratio, and preferably 1,000:0.5 to 1.0 as a molar ratio; however, the mixing ratio is not limited to this. When the mixing ratio is in this range, the polymer can be formed into a nano-sized hydrogel, and after reacting with nitric oxide, the hydrogel can be effectively swollen and rapidly dissociated.

The polymer in the form of a nano-sized hydrogel is very highly hydrophilic and can carry a drug or a protein. Furthermore, while conventional macro-sized or micro-sized hydrogels need to be transplanted into a site of lesion by surgery, the polymer according to the present invention is a nano-sized hydrogel and has an advantage that the polymer can be easily administered into the body without surgery, as an injectable preparation.

Furthermore, the hydrogel is such that even if it does not include any other biologically active substance, the hydrogel can scavenge nitric oxide and thus can alleviate or treat an inflammation or a disease caused by a high concentration of nitric oxide. That is, only the hydrogel per se can be used as a therapeutic agent.

On the other hand, when the hydrogel further includes a biologically active substance, the effect of treating an inflammation or a disease caused by a high concentration of nitric oxide can be further increased. Such a biologically active substance means a substance that is used for the treatment, remedy, prevention, diagnosis, or the like of diseases, and examples thereof include cells, proteins and peptides such as growth factors and hormones, nucleic acids, extracellular matrix substances, and drugs having a medical treatment function. In order to produce the hydrogel to include a biologically active substance, the biologically active substance can be prepared so as to be included in a certain solution, and this solution can be mixed with another solution so as to synthesize a hydrogel. In this case, the biologically active substance is in the form of being carried in a crosslinked polymer hydrogel thus formed. Also, two solutions each including a biologically active substance are mixed in a syringe, the mixture is delivered to a site of disease or lesion by using the syringe, and thereby production of a hydrogel including the biologically active substances can be induced with the passage of time. Therefore, as the polymer of the present invention is in the form of a hydrogel, the polymer can be used as a delivery system for a biologically active substance, a cell delivery system, or a drug delivery system. Furthermore, the polymer can also be used as a scaffold for tissue engineering or a cell therapeutic agent.

Examples of a drug as the biologically active substance to be carried by the hydrogel include an antibiotic agent, an anticancer agent, an anti-inflammatory analgesic agent, an antiviral agent, and an antibacterial agent. Examples of the antibiotic agent include antibiotic agents selected from derivatives and mixtures of tetracycline, minocycline, doxycycline, ofloxacin, levofloxacin, ciprofloxacin, clarithromycin, erythromycin, cefaclor, cefotaxime, imipenem, penicillin, gentamicin, streptomycin, and vancomycin. Examples of the anticancer agent include anticancer agents selected from derivatives and mixtures of methotrexate, carboplatin, taxol, cisplatin, 5-fluorouracil, doxorubicin, etoposide, paclitaxel, camptothecin, and cytosine arabinose. Examples of the anti-inflammatory agent include anti-inflammatory agents selected from derivatives and mixtures of indomethacin, ibuprofen, ketoprofen, piroxicam, flurbiprofen, and diclofenac. Examples of the antiviral agent include antiviral agents selected from derivatives and mixtures of acyclovir and robavin. Examples of the antibacterial agent include antibacterial agents selected from derivatives and mixtures of ketoconazole, itraconazole, fluconazole, amphotericin B, and griseofulvin.

Examples of the proteins and peptides that can be carried in the hydrogel and delivered to a living body include various physiologically active peptides such as hormones, cytokines, enzymes, antibodies, growth factors, transcriptional regulatory factors, blood factors, vaccines, structural proteins, ligand proteins, polysaccharides, receptors, cell surface antigens, and receptor antagonists, and derivatives and analogues thereof. Specific examples include bone growth factors, liver growth hormone, growth hormone-releasing hormone and peptides, interferons and interferon receptors (for example, interferon-α, interferon-β, interferon-γ, water-soluble type I interferon receptor), granulocyte colony stimulating factors (G-CSF), granulocyte-macrophage colony stimulating factors (GM-CSF), glucagon-like peptides (GLP-1 and the like), G-protein-coupled receptors, interleukins (for example, interleukin-1, interleukin-2, interleukin-3, interleukin-4, interleukin-5, interleukin-6, interleukin-7, interleukin-8, and interleukin-9) and interleukin receptors (for example, IL-1 receptors and IL-4 receptors), enzymes (for example, glucocerebrosidase, iduronate-2-sulfatase, alpha-galactosidase-A, agalsidase-alpha and agalsidase-beta, alpha-L-iduronidase, chitinase, butyrylcholinesterase, lipase, glutamate decarboxylase, imiglucerase, uricase, platelet-activating factor acetylhydrolase, neutral endopeptidase, and myeloperoxidase), interleukin- and cytokine-binding proteins (for example, IL-18 bp and TNF-binding proteins), macrophage activating factors, macrophage peptides, B cell factors, T cell factors, protein A, allergy inhibitors, tumor necrosis factor (TNF)-alpha inhibitors, cell necrosis glycoproteins, immunotoxins, lymphotoxins, tumor necrosis factors, tumor suppressors, metastasis growth factors, alpha-1 antitrypsin, albumin, alpha-lactalbumin, apolipoprotein-E, erythropoietin, highly glycosylated erythropoietin, angiopoietins, hemoglobin, thrombin, thrombin receptor activating peptides, thrombomodulin, blood factor, blood factor a, blood factor XIII, plasminogen activating factor, fibrin-binding peptides, urokinase, streptokinase, hirudin, protein C, C-reactive protein, renin inhibitors, collagenase inhibitors, superoxide dismutase, leptin, platelet-derived growth factors, epithelial growth factors, epidermal growth factors, angiostatin, angiotensin, bone morphogenetic proteins, bone morphogenetic stimulating proteins, calcitonin, insulin, atriopeptin, cartilage inducing factors, elcatonin, connective tissue activating factors, tissue factor pathway inhibitors, follicle stimulating hormone, luteinizing hormone, luteinizing hormone-releasing hormone, nerve growth factors (for example, nerve growth factors, ciliary neurotrophic factors, axogenesis factor-1, brain-natriuretic peptide, glial-derived neurotrophic factors, netrin, neutrophil inhibitors, neurotrophic factors, and neurturin), parathyroid hormone, relaxin, secretin, somatomedin, insulin-like growth factors, adrenocortical hormones, glucagon, cholecystokinin, pancreatic polypeptide, gastrin-releasing peptides, corticotropin-releasing factors, thyroid stimulating hormone, autotaxin, lactoferrin, myostatin, receptors (for example, TNFR (P75), TNFR (P55), IL-1 receptors, VEGF receptors, and B cell activating factor receptors), receptor antagonists (for example, IL1-Ra), cell surface antigens (for example, CD 2, 3, 4, 5, 7, 11a, 11b, 18, 19, 20, 23, 25, 33, 38, 40, 45, and 69), monoclonal antibodies, polyclonal antibodies, antibody fragments (for example, scFv, Fab, Fab', F(ab')2, and Fd), and virus-derived vaccine antigens.

Examples of the nucleic acid that can be physically carried in or chemically bonded to the above-described hydrogel and be delivered into the living body, include DNA, RNA, PNA, and oligonucleotides.

Examples of the extracellular matrix substance that can be physically carried in or chemically bonded to the above-described hydrogel and be delivered into the living body, include collagen, fibronectin, gelatin, laminin, and vitronectin.

Examples of the cell that can be physically carried in the hydrogel and be delivered into the living body include stem cells, fibroblasts, vascular endothelial cells, smooth muscle cells, nerve cells, cartilage cells, bone cells, skin cells, and Schwann cells.

The inflammatory disease is a disease in which nitric oxide in the body exhibits a condition of overexpression, and the disease is preferably any one selected from the group of rheumatoid arthritis, type I diabetes, and systemic lupus erythematosus, and more preferably rheumatoid arthritis. However, the inflammatory disease is not limited to these.

Rheumatoid arthritis is one of autoimmune diseases and is a disease caused by a high concentration of nitric oxide. Therefore, as the pharmaceutical composition according to the present invention includes a polymer that is responsive to nitric oxide and is capable of scavenging nitric oxide, the pharmaceutical composition can scavenge nitric oxide in an environment with a high concentration of nitric oxide, suppress cytokine-induced bone resorption by osteoclasts, and alleviate or treat rheumatoid arthritis by preventing cell death at the joints.

Furthermore, the pharmaceutical composition can further include a biologically active substance mentioned above, and the nitric oxide-sensitive acrylamide-based polymer having a structure represented by Chemical Formula 2 can carry the biologically active substance.

The pharmaceutical composition according to an embodiment of the present invention means a composition that is administered for a specific purpose. For the purpose of the present invention, the pharmaceutical composition of the present invention is used for the purpose of treating a disease or illness caused by overexpression of nitric oxide and includes a nitric oxide-sensitive acrylamide-based polymer, more preferably an acrylamide-based polymer including a crosslinking agent that is responsive to nitric oxide and is also capable of scavenging nitric oxide, and the pharmaceutical composition can further include a protein involved in nitric oxide scavenging and a pharmaceutically acceptable carrier, excipient, or diluent.

The above-described "pharmaceutically acceptable" carrier or excipient means a substance approved by a regulatory organization of the government, or a substance listed in the government-approved pharmacopoeia or any other generally approved pharmacopoeia for use for vertebrates, and more specially for human beings.

The pharmaceutical composition can be formulated into a suspension liquid, a solution, or an emulsion with an oily or aqueous carrier in order to be suitable for parenteral administration, can be produced in a solid form or a semisolid form, and can include a formulating agent such as a suspending agent, a stabilizer, a solubilizing agent, and/or a dispersant. The formulation may be sterilized and may be a liquid. This can be stabilized under the conditions for production and storage and can be preserved from the contaminating action of microorganisms such as bacteria and fungi. Alternatively, the pharmaceutical composition may be in the form of a sterilized powder for appropriate reconstitution using a carrier before use. The pharmaceutical composition may be stored in a unit dosage form and may be contained in a microneedle patch, an ample, another unit dosage container, or a multi-dosage container. Furthermore, the pharmaceutical composition may be stored simply in a freeze-dried (lyophilized) state, which requires adding of a sterilized liquid carrier, for example, water for injection, immediately before use. An injectable preparation and a suspension liquid that are used for instantaneous reconstitution can be produced using a sterilized powder, granules, or tablets.

According to some non-limiting embodiments, the pharmaceutical composition of the present invention may be formulated into a liquid or may be included in the form of microspheres in a liquid. According to some non-limiting embodiments, the pharmaceutical composition of the present invention includes a pharmaceutically acceptable compound and/or mixture as an active ingredient of the present invention at a concentration of 0.001 to 100,000 U/kg. Furthermore, according to some non-limiting embodiments, excipients appropriate for the pharmaceutical composition of the present invention include a preservative, a suspending agent, a stabilizer, a dye, a buffering agent, an antibacterial agent, an antifungal agent, and an isotonizing agent, for example, sugar or sodium chloride. The term "stabilizer" as used herein refers to a compound that is selectively used for the pharmaceutical composition of the present invention in order to increase the shelf-life. According to a non-limiting embodiment, the stabilizer may be a sugar, an amino acid, a compound, or a polymer. The pharmaceutical composition may include one or more pharmaceutically acceptable carriers. The carrier may be a solvent or a dispersing medium. Non-limiting examples of the pharmaceutically acceptable carrier include water, saline, ethanol, polyols (for example, glycerol, propylene glycol, and liquid polyethylene glycol), oil, and adequate mixtures of these. A parenteral formulation can be sterilized. Non-limiting examples of sterilization technique include filtration through a bacteria-suppressing filter, terminal sterilization, incorporation of a sterilizing preparation, irradiation with radiation, injection of a sterilizing gas, heating, vacuum drying, and freeze-drying.

According to an embodiment of the present invention, the term administration means introduction of the composition of the present invention to a patient by any appropriate method, and regarding the route of administration, the composition of the present invention can be administered through any general route so long as the composition can arrive at an intended tissue. Oral administration, intraperitoneal administration, intravenous administration, intramuscular administration, subcutaneous administration, intradermal administration, intranasal administration, intrapulmonary administration, intrarectal administration, intracavitary administration, intraperitoneal administration, and intrathecal administration can be achieved. However, in the case of the pharmaceutical composition including a nitric oxide-sensitive acrylamide-based polymer of the present invention, since the pharmaceutical composition is in the form of a nano-sized hydrogel, the pharmaceutical composition can be parenterally administered and can therefore be administered as an injectable preparation.

The therapeutic method of the present invention can include administering a pharmaceutically effective amount of the above-described pharmaceutical composition. According to the present invention, the effective amount can be regulated according to various factors including the type of disease, severity of the disease, the type and contents of the active ingredient and other components included in the composition, the type of dosage form, the age, body weight, general health condition, gender, and diet of the patient, the administration time, the administration route, the secretion rate of the composition, the duration of treatment, and simultaneously used drugs.

Hereinafter, preferable Examples will be described in order to assist understanding of the present invention. However, the following Examples are only for illustrating the present invention, and it should be clear to those ordinarily skilled in the art that various modifications and alterations can be made within the scope of technical idea of the present invention. It is also definitely clear that such modifications and alterations are included in the scope of the attached claims.

Manufacturing Example 1: Synthesis of Crosslinking Agent that can be Degraded by Reaction with Nitric Oxide (Nitric Oxide-Cleavable Crosslinker)

N,N-(2-amino-1,4-phenylene) diacrylamide, which is a crosslinking agent that can be degraded by a reaction with nitric oxide, was synthesized as shown in FIG. 1. Specifically, the nitric oxide-cleavable crosslinker was synthesized by the following four-stage procedure.

In a first stage, di-t-butyl dicarbonate (2.85 mg, 13.06 mmol) was added dropwise to a reaction solution obtained by dissolving 4-nitro-o-phenylenediamine (1 g, 6.53 mmol) and guanidine hydrochloride (15 mol %) in 20 ml of ethanol, and then the mixture was vigorously stirred for 40 hours while the temperature was maintained at 35° C. to 40° C. After completion of the reaction, the organic solvent in the reaction solution as evaporated under reduced pressure, the residue was extracted three times with ethyl acetate and dried, and then the dried residue was purified by silica gel column chromatography (yield: 74% by weight, 1.22 g).

In a second stage, in a nitrogen atmosphere, a carbon catalyst loaded with 10% by weight of palladium (10% by weight Pd/C, 60 mg) was added to a solution (in anhydrous tetrahydrofuran (dry THF), 10 ml) of the compound (0.6 g) obtained in the first stage, subsequently the nitrogen atmosphere was changed to a hydrogen atmosphere (40 psi), and the mixture was stirred for 36 hours at 25° C. After completion of the reaction, Pd/C was removed by filtration using Celite 545AW, the filtrate was dried, and a compound was obtained without further purification (yield: 96% by weight, 423 mg).

In a third stage, acryloyl chloride (648.05 mg, 7.16 mmol) was added dropwise to a reaction solution obtained by dissolving the compound (400 mg, 1.79 mmol) obtained in the second stage and triethylamine (723.16 mg, 7.16 mmol) in anhydrous THF at 25° C., and then the mixture was vigorously stirred for 24 hours at 25° C. After completion of the reaction, the organic solvent in the reaction solution was evaporated under reduced pressure, the residue was extracted three times with ethyl acetate and dried, and then the dried residue was purified by alumina chromatography (yield: 64% by weight, 379 mg).

In a fourth stage, in an ice bath, 3 ml of a 4 M HCl-dioxane solution was added to a solution (in anhydrous THF, 3 ml) of compound 3 (200 mg, 0.60 mmol), and then the mixture was vigorous stirred for 24 hours at 25° C. After completion of the reaction, the organic solvent in the reaction solution was evaporated under reduced pressure, the residue was extracted three times with ethyl acetate and dried, and then the dried residue was purified by alumina chromatography (yield: 21% by weight, 29.11 mg).

4-Nitro-o-phenylenediamine, which is a starting substance, contains an o-phenylenediamine moiety that reacts with nitric oxide. The amino group at C-2 of 4-nitro-o-phenylenediamine was selectively subjected to Boc-protection using guanidine hydrochloride (guanidine HCl) as a catalyst. Next, 4-$NO_2$ in 4-nitro-o-phenylenediamine was reduced into 4-$NH_7$. Next, two amino groups at C-1 and C-4 were bonded to acryloyl chloride, and thereby vinyl groups capable of radical polymerization were introduced. Subsequently, Boc at C-2 was removed using hydrochloric acid. The crosslinking agent synthesized as such was analyzed by $^1$H-NMR to check the structure, and the spectrum is shown in FIG. 2.

Manufacturing Example 2: Production of Nitric Oxide-Sensitive Hydrogel

Polymerization was carried out using 10 μl of a 5% (w/v) solution of nitric oxide-cleavable crosslinker (0.0312 mg) produced in Production Example 1, 10 μl of a 20% (w/v) solution of an acrylamide monomer, 1 μl of a 10% (w/v) solution of ammonium persulfate as an initiator, and 1 μl of a 5% (w/v) solution of tetramethylethylenediamine as a catalyst. At this time, polymerization was carried out for 3 minutes at 25° C. A polymer thus polymerized was formed in the form of a nano-sized hydrogel.

Example 1: A nano-sized hydrogel was produced in the same manner as in Production Example 2.

Comparative Example 1: A hydrogel was produced in the same manner as in Production Example 2, except that polymerization was carried out by incorporating N,N'-methylene bisacrylamide (BIS) instead of the nitric oxide-cleavable crosslinker.

Experimental Example 1: Examination of Size and Distribution of Nitric Oxide-Sensitive Hydrogel The size and distribution of the hydrogel were checked using transmission electron microscopy (TEM) and dynamic light scattering (DLS). It was verified that the hydrogel crosslinked together with the nitric oxide-cleavable crosslinker was a nano-sized hydrogel having a diameter of 20 to 100 nm, and it was also verified by TEM and DLS that when nitric oxide was added to the hydrogel of Example 1, the size of the hydrogel increased (see FIG. 3 and FIG. 4). On the other hand, Comparative Example 1, which was a hydrogel crosslinked together with N,N'-methylene bisacrylamide (BIS), did not show any change in the size even if nitric oxide was added, and this implies that the hydrogel was not responsive to nitric oxide. Accordingly, it was verified that the polymer according to the present invention was responsive to nitric oxide.

Experimental Example 2: Examination of Nitric Oxide Scavenging Ability of Nitric Oxide-Cleavable Crosslinker In order to check whether the nitric oxide-cleavable crosslinker (NOCCL) produced according to Production Example 1 can actually scavenge nitric oxide, Griess reagent was used, and 100 μM nitric oxide and 10 μM nitric oxide were treated to check the scavenging ability of the nitric oxide-cleavable crosslinker. At this time, N,N'-methylene bisacrylamide (BIS) was used as a comparative group, and water was used as a control group. The results for these are presented in FIG. 5.

As shown in FIG. 5, it was verified that the nitric oxide-cleavable crosslinker scavenged 30% or more of nitric oxide as compared to the comparative group. Particularly, the nitric oxide-cleavable crosslinker exhibited a scavenging ability of 50% or more even when the crosslinker was used to treat a high concentration (100 μM) of nitric oxide. Accordingly, it was verified that the polymer according to the present invention contained a chemical structure that can scavenge nitric oxide.

Experimental Example 3: Evaluation of Hemolysis of Nitric Oxide-Sensitive Hydrogel In order to check whether the nitric oxide-sensitive hydrogel has in vivo stability after being administered into the body, first, red blood cells were separated from the blood collected from mice. A DPBS solution including 1 mg/mL Example 1, the nitric oxide-cleavable crosslinker (NOCCL), and acrylamide was introduced into 1×$10^8$ cells of the red blood cells thus prepared, and the mixture was thoroughly mixed. This solution was left to stand for 4 hours in a constant temperature tank at 37° C. Next, the solution was centrifuged, subsequently the supernatant was transferred onto a 96-well plate, and the absorbance at 450 nm was measured to calculate the degree of hemolysis. The results are presented in FIG. 6.

As shown in FIG. 6, Example 1 and the nitric oxide-cleavable crosslinker did not cause hemolysis, while hemolysis occurred up to 99% in acrylamide. This implies that the acrylamide-based polymer according to the present invention has in vivo stability.

Experimental Example 4: Verification of therapeutic effect for rheumatoid arthritis using nitric oxide-sensitive hydrogel First, animal models were prepared, and 6- to 7-week old male DBA/1J mice were used as test animals. Type II collagen (CII) was dissolved in a 0.1 N acetic acid solution to a concentration of 4 mg/ml, and then the solution was dialyzed with a dialysis buffer solution (50 mM Tris, 0.2 N NaCl). The solution was mixed with the same amount of Complete Freund's adjuvant (CFA, Chondrex) containing *M. tuberculosis*, and then the mixture was subcutaneously injected into the caudal basal part of each mouse such that 100 μl of the immunogen was injected (that is, 200 μg/100 μl) (first injection). Two weeks after the first injection, the same type II collagen was mixed with the same amount of Incomplete Freund's adjuvant (IFA, Chondrex), and then 100 μl of the mixture (that is, 200 μg/100 μl) was injected to one hindlimb and one forelimb (footpads)) (second injection). After the second injection, 30 μl (forelimb) each and 50 μl (hindlimb) each of Example 1, Comparative Example 1, and a buffer solution (saline solution) at a concentration of 0.25 mg/kg were respectively injected two times in total into the footpads of different mice at an interval of 7 days, and 30 μl (forelimb) each and 50 μl (hindlimb) each of dexamethasone at a concentration of 0.0025 μg/kg was respectively injected two times in total into the footpads of different mice at an interval of 7 days. Next, observation of the hindlimb footpads and the forelimb footpads of the mice was made in Week 2 and Week 5 from the time point of first administration of Example 1 as the starting point (FIG. 7).

Five animals were grouped in each group, and the evaluation of rheumatoid arthritis was conducted up to 5 weeks. For an in vitro test, each animal was victimized at a time point where the arthritis index showed significant differences, and the degrees of pathological activity of arthritis in the blood and the articular tissue were investigated.

As shown in FIG. 7, when Example 1 was administered by injection, edema or rubefaction in the footpads did not occur, whereas when Comparative Example 1 or the buffer solution was administered by injection, severe edema and rubefaction occurred. On the other hand, when dexamethasone, which has been known as a therapeutic agent for rheumatoid arthritis, was administered by injection, edema or rubefaction in the footpads almost did not occur in Week 2; however, it was recognized that slight rubefaction occurred in Week 5. Therefore, it was verified that Example 1 has a superior effect of treating or alleviating rheumatoid arthritis compared to dexamethasone.

Experimental Example 5: Verification of therapeutic effect for rheumatoid arthritis using nitric oxide-sensitive hydrogel (2)

Collagen-induced arthritis (CIA) animal models were prepared in the same manner as in Experimental Example 4, and 30 μl (forelimb) each and 50 μl (hindlimb) each of Example 1, Comparative Example 1, and a buffer solution (saline solution) at a concentration of 0.25 mg/kg were respectively injected two times in total into the footpads of different mice at an interval of 7 days, and 30 μl (forelimb) each and 50 μl (hindlimb) each of dexamethasone at a concentration of 0.0025 μg/kg was respectively injected two times in total into the footpads of different mice at an interval of 7 days. Next, the severity of articular inflammation was evaluated once a week from the time point of first administration as the starting point, and observation was made up to five weeks. The results for this are presented in FIG. 8. Regarding the evaluation of arthritis at this time, the medical scores obtained from the four legs for each animal according to the following criteria on the basis of the average arthritis index established by Rossoliniec et al. were combined, and the sum was divided by 5 to obtain an average value. Here, the medical scores and criteria according to the arthritis evaluation are as follows.

0 points: No edema or tumefaction occurred.
1 point: Light edema and rubefaction localized in the foot or the ankle joint
2 points: Light edema and rubefaction extending from the ankle joint to the metatarsal
3 points: Edema and rubefaction of medium degree extending from the ankle joint to the metatarsal
4 points: Edema and rubefaction extending from the ankle joint to the entire leg Since the highly arthritis index per animal was 4 points, the highest disease index per mouse was 16.

As shown in FIG. 8, it was verified that when Example 1 was administered by injection, the disease index was the lowest compared to other experiment groups, while when Comparative Example 1 or a buffer solution was administered by injection, the disease index further increased as time passed. On the other hand, when dexamethasone that has been known as a therapeutic agent for rheumatoid arthritis was administered by injection, it was found that dexamethasone alleviated rheumatoid arthritis similarly to Example 1 up to two weeks; however, the effect was deteriorated after two weeks. Therefore, it was verified that Example 1 has a superior effect in treating or alleviating rheumatoid arthritis compared to dexamethasone.

The invention claimed is:

1. A pharmaceutical composition for preventing or treating an inflammatory disease, comprising a nitric oxide-sensitive acrylamide-based polymer, wherein the acrylamide-based polymer is produced using:
    an acrylamide-based monomer;
    a crosslinking agent having a structure represented by the following Chemical Formula 1;
    a radical initiator; and
    a catalyst,
    wherein the acrylamide-based polymer has a structure represented by the following Chemical Formula 2:

[Chemical Formula 1]

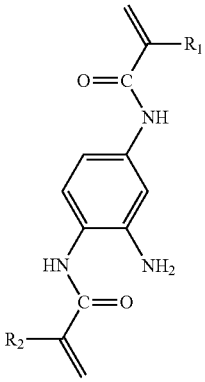

[Chemical Formula 2]

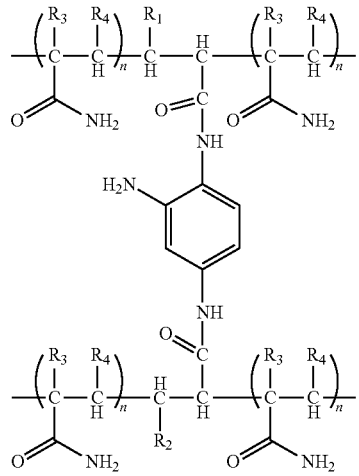

wherein $R_1$, $R_2$, $R_3$, and $R_4$ each independently represent a hydrogen atom or a C1-C10 substituted or unsubstituted alkyl group; and n represents an integer from 1 to 1,000.

2. The pharmaceutical composition for preventing or treating an inflammatory disease according to claim 1, wherein $R_1$, $R_2$, $R_3$, and $R_4$ each independently represent a hydrogen atom.

3. The pharmaceutical composition for preventing or treating an inflammatory disease according to claim 1, wherein the acrylamide-based monomer is one or more selected from the group consisting of acrylamide, (meth)acrylamide, N-isopropylacrylamide, N-tertiary butyl acrylamide, 3-hydroxypropyl (meth)acrylamide, 4-hydroxybutyl (meth)acrylamide, 6-hydroxyhexyl (meth) acrylamide, 8-hydroxyoctyl (meth)acrylamide, 2-hydroxyethylhexyl (meth)acrylamide, N-methylol (meth) acrylamide, N,N-dimethylol (meth) acrylamide, N-methoxymethyl (meth) acrylamide, and N-propoxymethyl (meth) acrylamide.

4. The pharmaceutical composition for preventing or treating an inflammatory disease according to claim 1, wherein the polymer is in the form of a hydrogel.

5. The pharmaceutical composition for preventing or treating an inflammatory disease according to claim 4, wherein the diameter of the hydrogel is 10 nm to 500 nm.

6. The pharmaceutical composition for preventing or treating an inflammatory disease according to claim 1, wherein the pharmaceutical composition is an injectable preparation.

7. The pharmaceutical composition for preventing or treating an inflammatory disease according to claim 1, wherein the inflammatory disease is a disease in which nitric oxide in the body exhibits a condition of overexpression.

8. The pharmaceutical composition for preventing or treating an inflammatory disease according to claim 1, wherein the inflammatory disease is rheumatoid arthritis.

9. The pharmaceutical composition for preventing or treating an inflammatory disease according to claim 1, wherein the pharmaceutical composition further comprises a biologically active substance, and the nitric oxide-sensitive acrylamide-based polymer is carrying the biologically active substance.

\* \* \* \* \*